(12) United States Patent
Haddad et al.

(10) Patent No.: US 8,946,418 B1
(45) Date of Patent: Feb. 3, 2015

(54) CHIRAL NITROGEN-PHOSPHORUS LIGANDS AND THEIR USE FOR ASYMMETRIC HYDROGENATION OF ALKENES

(71) Applicants: Nizar Haddad, Danbury, CT (US); Bo Qu, Brookfield, CT (US); Jolaine Savoie, Danbury, CT (US); Chris Hugh Senanayake, Brookfield, CT (US); Xudong Wei, Ridgefield, CT (US)

(72) Inventors: Nizar Haddad, Danbury, CT (US); Bo Qu, Brookfield, CT (US); Jolaine Savoie, Danbury, CT (US); Chris Hugh Senanayake, Brookfield, CT (US); Xudong Wei, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/327,076

(22) Filed: Jul. 9, 2014

Related U.S. Application Data

(60) Provisional application No. 61/987,187, filed on May 1, 2014, provisional application No. 61/844,567, filed on Jul. 10, 2013.

(51) Int. Cl.
*C07F 15/00* (2006.01)
*C07F 9/6571* (2006.01)
*B01J 31/22* (2006.01)

(52) U.S. Cl.
CPC ........ *C07F 15/0033* (2013.01); *C07F 9/657163* (2013.01); *B01J 31/2295* (2013.01); *B01J 2231/64* (2013.01)
USPC .............................................. 546/2; 546/22

(58) Field of Classification Search
USPC ...................................... 546/2, 22
See application file for complete search history.

(56) References Cited

U.S. PATENT DOCUMENTS 8,552,212 B2 * 10/2013 Qu et al. .................... 556/18

FOREIGN PATENT DOCUMENTS

WO  2011056737 A1  5/2011

OTHER PUBLICATIONS

Fandrick, D.R. et al.: Copper catalyzed asymmetric propargylation of aldehydes. J. Am. Chem. Soc., vol. 132, pp. 7600-7601, 2010.*
International Search Report and Written Opinion for PCT/US2014/045969 mailed Sep. 9, 2014.
Qu, B. et al., "Synthesis of Pyridyl-dihydrobenzooxaphosphole Ligands and Their Application in Asymmetric Hydrogenation of Unfunctionalized Alkenes." The Journal of Organic Chemistry, 2014, vol. 79, No. 3, pp. 993-1000.

* cited by examiner

*Primary Examiner* — Charanjit Aulakh
(74) *Attorney, Agent, or Firm* — Michael P. Morris; David L. Kershner

(57) ABSTRACT

The invention relates to a series of novel chiral nitrogen-phosphorus ligands of formulae (Ia) and (Ib):

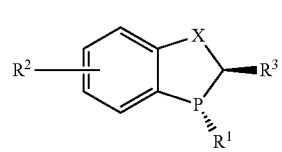

Ia

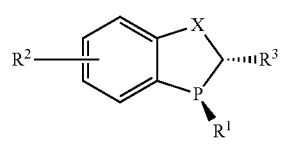

Ib wherein $R^1$-$R^3$ and X are as defined herein. The invention also relates to chiral metal complexes prepared with these chiral nitrogen-phosphorus ligands. The chiral metal complexes are useful as catalysts for carrying out asymmetric hydrogenation.

19 Claims, No Drawings

CHIRAL NITROGEN-PHOSPHORUS LIGANDS AND THEIR USE FOR ASYMMETRIC HYDROGENATION OF ALKENES

FIELD OF THE INVENTION

The present invention relates to a series of novel chiral nitrogen-phosphorus ligands and their metal complexes as catalysts for applications in asymmetric hydrogenation of alkenes. More particularly, the present invention relates to the transition metal complexes of these novel nitrogen-phosphine ligands and their use as catalysts in asymmetric hydrogenation of alkenes.

BACKGROUND OF THE INVENTION

The increasing demand to produce enantiomerically pure pharmaceuticals, agrochemicals, flavors, and other fine chemicals has advanced the field of asymmetric catalytic technologies. Development of efficient asymmetric metal-catalyzed transformations has played a central role for the advancement of asymmetric catalysis (Jacobsen, E. N., Pfaltz, A., Yamamoto, H., Eds., Comprehensive Asymmetric Catalysis, Springer, Berlin, 1999; Ojima, I., Ed, *Catalytic Asymmetric Synthesis*, VCH, New York, 1993; and Noyori, R. *Asymmetric Catalysis In Organic Synthesis*, John Wiley & Sons, Inc., New York, 1994). Among most successful transformations are asymmetric hydrogenation, asymmetric epoxidation and dihydroxylations, which were awarded Nobel Prizes in 2001 for their efficiency, simplicity, and practicality. Chiral ligand design has become and will continue to be of great importance for developing new efficient asymmetric metal-catalyzed reactions.

Asymmetric hydrogenation utilizing molecular hydrogen to reduce prochiral olefins, ketones, and imines has become one of most efficient methods for constructing chiral compounds. It also accounts for the major asymmetric catalytic transformation at commercial scales. Development of efficient chiral phosphorus ligands is essential for the success of asymmetric hydrogenation. Known chiral phosphorus ligands in this field include Knowles' DIPAMP [Knowles, W. S. *Acc. Chem. Res.* 1983, 16, 106], Kagan's DIOP [Kagan et al, *J. Am. Chem. Soc.* 1972, 94, 6429], Noyori's BINAP [Noyori, R. *Chem. Soc. Rev.* 1989, 18, 187], Burk's Duphos and BPE [Burk, M. J. et al, Organometallics 1990, 9, 2653; Burk, M. J. et al, *Angew. Chem., Int. Ed. Engl.* 1990, 29, 1462], Imamoto's BisP* [Imamoto, T. et al, J. Am. Chem. Soc. 1997, 119, 1799], Zhang's PennPhos [Zhang, X. et al, *Angew. Chem. Int. Ed. Engl.* 1999, 38, 516] and TangPhos [US2004/0229846 and Zhang, X. et al, *Angew. Chem. Int. Ed.* 2002, 41, 1613.], Pfizer's trichickenfootphos [WO2005/087370 and Hoge, G. et al, *J. Am. Chem. Soc.* 2004, 126, 5966].

Recently, we described a novel series of BIBOP and POP ligands which were derived from a rigid modular P-chiral dihydrobenzooxaphosphole core, in WO 2011/056737. These ligands showed high enantioselectivity in Rhodium catalyzed asymmetric hydrogenation of functionalized olefins, such as enamides and amino acids.

Although tremendous progress has been made in the field of asymmetric hydrogenation and many efficient chiral ligands have been developed, the design of new efficient ligands continues to be important since there is no universal ligand for hydrogenation of various kinds of prochiral substrates.

BRIEF SUMMARY OF THE INVENTION

We have developed a series of air-stable, tunable, novel and efficient chiral nitrogen-phosphorus ligands that have shown excellent reactivity and enantioselectivity in asymmetric hydrogenation. High enantioselectivity has been achieved in asymmetric hydrogenation of alkenes.

DETAILED DESCRIPTION OF THE INVENTION

Abbreviations

[IrCl(COD)]$_2$=chloro(1,5-cyclooctadiene)iridium (I) dimer
B(C$_6$H$_5$)$_4$$^-$=tetraphenylborate
B[3,5-(CF$_3$)$_2$C$_6$H$_3$]$_4$$^-$ (BArF$^-$)=tetrakis[(3,5-trifluoromethyl)phenyl]borate
BF$_4$$^-$=tetrafluoroborate
DCM=dichloromethane
EtOAc=ethyl acetate
EtOH=ethanol
HOAc=acetic acid
IPA=isopropyl alcohol
LDA=lithium diisopropylamide
MeOH=methanol
MeTHF=2-methyltetrahydrofuran
NaBArF=sodium tetrakis[(3,5-trifluoromethyl)phenyl]borate
NaHMDS=sodium hexamethyldisilazide
PF$_6$$^-$=hexafluorophosphate
PMHS=polymethylhydrosilane
SbF$_6$$^-$=hexafluoroantimonate
TfO$^-$=trifluoromethanesulfonate
THF=tetrahydrofuran
Ti(OiPr)$_4$=titanium tetraisopropoxide In its broadest embodiments, the present invention relates to novel nitrogen-phosphine ligands, novel metal complexes containing the novel nitrogen-phosphine ligands of the invention, and methods of using the novel metal complexes to carry out asymmetric hydrogenations as described below.

The Nitrogen-Phosphine Ligands of the Invention

As noted above, in one embodiment, the present invention relates to a compound of formula (Ia), (Ib), or a mixture thereof ("the nitrogen-phosphine ligand of the invention"):

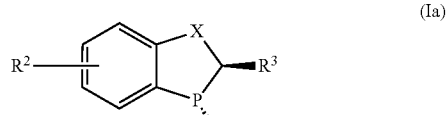
(Ia)

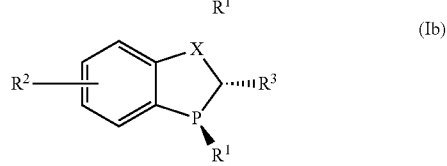
(Ib)

wherein:
X is O, S, or —NR$^5$;
R$^1$ is —(C$_1$-C$_6$)alkyl, —CF$_3$, —(C$_3$-C$_{10}$)carbocyclyl, -(5- to 11-membered)heterocarbocyclyl, —(C$_6$-C$_{14}$)aryl, -(5 to 11-membered)heteroaryl, or ferrocenyl; wherein said —(C$_3$-C$_{10}$)carbocyclyl, -(5- to 11-membered)heterocarbocyclyl, —(C$_6$-C$_{14}$)aryl and -(5 to 11-membered)heteroaryl of said R$^1$ is optionally substituted with 1 to 3 substituents independently selected from —O(C$_1$-C$_6$)alkyl, —(C$_1$-C$_6$)alkyl, and —CF$_3$;

$R^2$ is H, —O($C_1$-$C_6$)alkyl, —($C_1$-$C_6$)alkyl, —($C_3$-$C_{10}$)carbocyclyl, -(5- to 11-membered)heterocarbocyclyl, —($C_6$-$C_{14}$)aryl, -(5 to 11-membered)heteroaryl, —NR$^5$R$^6$, or —SR$^5$; wherein said —($C_3$-$C_{10}$)carbocyclyl, -(5- to 11-membered)heterocarbocyclyl, —($C_6$-$C_{14}$)aryl, and -(5 to 11-membered)heteroaryl of said $R^2$ is optionally substituted with 1 to 3 substituents independently selected from —O($C_1$-$C_6$)alkyl, —($C_1$-$C_6$)alkyl, and —CF$_3$;

$R^3$ is —($C_1$-$C_6$)alkyl substituted with 1 to 3 (5- to 6-membered)heteroaryl; wherein the (5- to 6-membered)heteroaryl ring is optionally substituted with 1 to 3 $R^4$ substituents independently selected from —O($C_1$-$C_6$)alkyl, —N—($C_1$-$C_6$alkyl)$_2$, —($C_1$-$C_6$)alkyl, phenyl, (5- to 11-membered)heteroaryl and —CF$_3$;

or $R^3$ is (5- to 11-membered)heteroaryl optionally substituted with 1 to 3 $R^4$ substituents independently selected from —O($C_1$-$C_6$)alkyl, —N—($C_1$-$C_6$alkyl)$_2$, —($C_1$-$C_6$)alkyl, phenyl, (5- to 11-membered)heteroaryl and —CF$_3$;

$R^5$ and $R^6$ are each independently H, —($C_1$-$C_6$)alkyl, —CF$_3$, —($C_3$-$C_{10}$)carbocyclyl, -(5- to 11-membered)heterocarbocyclyl, —($C_6$-$C_{10}$)aryl, or -(5 to 11-membered)heteroaryl; wherein each —($C_1$-$C_6$)alkyl, —CF$_3$, —($C_3$-$C_{10}$)carbocyclyl, -(5- to 11-membered)heterocarbocyclyl, —($C_6$-$C_{10}$)aryl, and -(5 to 11-membered)heteroaryl of said R$^5$ and R$^6$ is optionally independently substituted with 1 to 3 substituents independently selected from halo, —O($C_1$-$C_6$)alkyl, —($C_1$-$C_6$)alkyl, and —CF$_3$.

In another embodiment, the invention relates to a compound of formula (Ia), (Ib), or a mixture thereof, according to the embodiment described immediately above, wherein X is O.

In another embodiment, the invention relates to a compound of formula (Ia), (Ib), or a mixture thereof, according to the broadest embodiment described above, wherein X is S.

In another embodiment, the invention relates to a compound of formula (Ia), (Ib), or a mixture thereof, according to the broadest embodiment described above, wherein X is NR$^5$.

In another embodiment, the invention relates to a compound of formula (Ia), (Ib), or a mixture thereof, according to any of the preceding embodiments, wherein R$^1$ is —($C_1$-$C_6$) alkyl selected from —CH$_3$, —CH$_2$CH$_3$, —CH(CH$_3$)$_2$, —C(CH$_3$)$_3$, —C(CH$_2$CH$_3$)$_3$, or —C(CH$_2$CH$_3$)(CH$_3$)$_2$.

In another embodiment, the invention relates to a compound of formula (Ia), (Ib), or a mixture thereof, according to the broadest embodiment described above, wherein R$^1$ is —($C_3$-$C_{10}$)carbocyclyl selected from cyclopentyl, cyclohexyl, and 1-adamantyl.

In another embodiment, the invention relates to a compound of formula (Ia), (Ib), or a mixture thereof, according to the broadest embodiment described above, wherein R$^1$ is —($C_6$-$C_{14}$)aryl selected from phenyl, ortho-tolyl, para-tolyl, 3,5-dimethylphenyl, 3,5-di-t-butylphenyl, 3,5-di-CF$_3$-phenyl, ortho-CF$_3$-phenyl, ortho-anisyl, and naphthyl.

In another embodiment, the invention relates to a compound of formula (Ia), (Ib), or a mixture thereof, according any of the preceding embodiments, wherein R$^2$ is H, —CH$_3$ or —OCH$_3$.

In another embodiment, the invention relates to a compound of formula (Ia), (Ib), or a mixture thereof, according to the broadest embodiment described above wherein R$^2$ is phenyl, naphthyl or anthracene, each optionally substituted with 1 to 3 substituents independently selected from —O($C_1$-$C_6$) alkyl, —($C_1$-$C_6$)alkyl, and —CF$_3$.

In another embodiment, the invention relates to a compound of formula (Ia), (Ib), or a mixture thereof, according to the broadest embodiment described above, wherein R$^3$ is —($C_1$-$C_6$)alkyl substituted with 1 to 3 (5- to 6-membered)heteroaryl; wherein the (5- to 6-membered)heteroaryl ring is optionally substituted with 1 to 3 R$^4$ substituents independently selected from —O($C_1$-$C_6$)alkyl, —($C_1$-$C_6$)alkyl, phenyl and —CF$_3$.

In another embodiment, the invention relates to a compound of formula (Ia), (Ib), or a mixture thereof, according to the embodiment described immediately above, wherein R$^3$ is —CH$_2$(chiral oxazoline) or —CH$_2$(ortho-substituted pyridine), each optionally substituted with 1 to 3 R$^4$ substituents independently selected from —O($C_1$-$C_6$)alkyl, —($C_1$-$C_6$) alkyl, phenyl and —CF$_3$.

In another embodiment, the invention relates to a compound of formula (Ia), (Ib), or a mixture thereof, according to the broadest embodiment described above, wherein R$^3$ is a -(5- to 6-membered)heteroaryl selected from ortho-substituted pyridine, oxazoline, and chiral oxazoline, each optionally substituted with 1 to 3 R$^4$ substituents independently selected from —O($C_1$-$C_6$)alkyl, —($C_1$-$C_6$)alkyl, phenyl and —CF$_3$.

In another embodiment, the invention relates to compound (Ia) of formula:

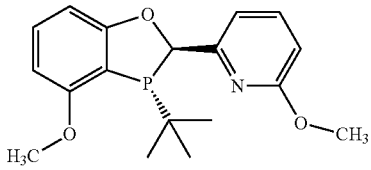 [SMILES: COc1cccc([C@@H]2Oc3cccc(OC)c3[P@@]2C(C)(C)C)n1]

In another embodiment, the invention relates to compound (Ib) of formula:

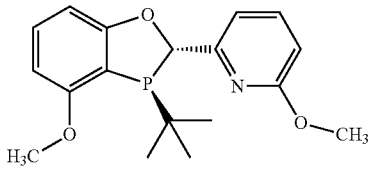 [SMILES: COc1cccc([C@H]2Oc3cccc(OC)c3[P@]2C(C)(C)C)n1]

The Metal Complexes of the Invention

As noted above, the invention relates to complexes formed between a transition metal and the nitrogen-phosphine ligands of the invention. Accordingly, in one embodiment, the invention relates to a metal complex of formula (IIa), (IIb), ("the metal complexes of the invention"):

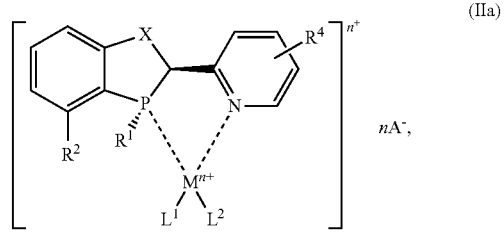

-continued

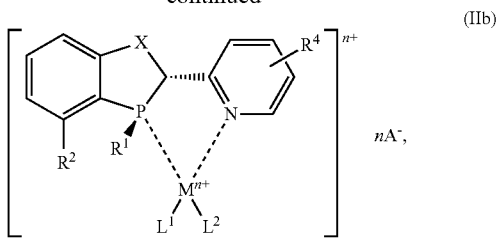

wherein
M is a transition metal selected from Co, Ni, Pd, Pt, Cu, Ag, Au, Ru, Fe, Rh and Ir;
$A^-$ is a counter anion;
n is the oxidation state of the transition metal M;
$L^1$ and $L^2$ are each olefins, or $L^1$ and $L^2$ together represent a diolefin;
X is O, S, or —$NR^5$;
$R^1$ is —$(C_1-C_6)$alkyl, —$CF_3$, —$(C_3-C_{10})$carbocyclyl, -(5- to 11-membered)heterocarbocyclyl, —$(C_6-C_{14})$aryl, -(5 to 11-membered)heteroaryl, or ferrocenyl; wherein said —$(C_3-C_{10})$carbocyclyl, -(5- to 11-membered)heterocarbocyclyl, —$(C_6-C_{14})$aryl and -(5 to 11-membered)heteroaryl of said $R^1$ is optionally substituted with 1 to 3 substituents independently selected from —$O(C_1-C_6)$alkyl, —$(C_1-C_6)$alkyl, and —$CF_3$;
$R^2$ is H, —$O(C_1-C_6)$alkyl, —$(C_1-C_6)$alkyl, —$(C_3-C_{10})$carbocyclyl, -(5- to 11-membered)heterocarbocyclyl, —$(C_6-C_{14})$aryl, -(5 to 11-membered)heteroaryl, —$NR^5R^6$, or —$SR^5$; wherein said —$(C_3-C_{10})$carbocyclyl, -(5- to 11-membered)heterocarbocyclyl, —$(C_6-C_{14})$aryl, and -(5 to 11-membered)heteroaryl of said $R^2$ is optionally substituted with 1 to 3 substituents independently selected from —$O(C_1-C_6)$alkyl, —$(C_1-C_6)$alkyl, and —$CF_3$;
$R^4$ is selected from —$O(C_1-C_6)$alkyl, —$(C_1-C_6)$alkyl, phenyl and —$CF_3$;
$R^5$ and $R^6$ are each independently H, —$(C_1-C_6)$alkyl, —$CF_3$, —$(C_3-C_{10})$carbocyclyl, -(5- to 11-membered)heterocarbocyclyl, —$(C_6-C_{10})$aryl, or -(5 to 11-membered)heteroaryl; wherein each —$(C_1-C_6)$alkyl, —$CF_3$, —$(C_3-C_{10})$carbocyclyl, -(5- to 11-membered)heterocarbocyclyl, —$(C_6-C_{10})$aryl, and -(5 to 11-membered)heteroaryl of said $R^5$ and $R^6$ is optionally independently substituted with 1 to 3 substituents independently selected from halo, —$O(C_1-C_6)$alkyl, —$(C_1-C_6)$alkyl, and —$CF_3$.

In another embodiment, the invention relates to a metal complex of the invention wherein M is Ir and n is 1.

In another embodiment, the invention relates to a metal complex of the invention according to any of the two embodiments described immediately above, wherein $A^-$ is, $BF_4^-$, $SbF_6^-$, $TfO^-$, $B(C_6H_5)_4^-$, $B[3,5-(CF_3)_2C_6H_3]_4^-$ ($BArF^-$), or $PF_6^-$.

In another embodiment, the invention relates to a metal complex of the invention according to any of the three embodiments described immediately above, wherein M is Ir, $A^-$ is $BArF^-$, and n is 1.

In another embodiment, the invention relates to a metal complex of the invention according to any of the four embodiments described immediately above, wherein $R^1$ is —$C(CH_3)_3$, and $R^2$ is —$OCH_3$, or —$(C_6-C_{14})$aryl; wherein said —$(C_6-C_{14})$aryl is optionally substituted with 1 to 3 substituents independently selected from —$O(C_1-C_6)$alkyl, —$(C_1-C_6)$alkyl, and —$CF_3$;

In another embodiment, the invention relates to a metal complex of the invention wherein $L^1$ and $L^2$ together represent a diolefin selected from norbornadiene and cyclooctadiene.

In another embodiment, the invention relates to a metal complex of the invention, wherein the metal complex is of formula (IIa).

In another embodiment, the invention relates to a metal complex of the invention according to the embodiment immediately above, wherein M is Ir, $A^-$ is $BArF^-$; and n is 1.

In another embodiment, the invention relates to a metal complex of the invention according to the embodiment immediately above, wherein $L^1$ and $L^2$ together represent a diolefin selected from norbornadiene and cyclooctadiene.

In another embodiment, the invention relates to a metal complex of the invention, wherein the metal complex is of formula (IIb).

In another embodiment, the invention relates to a metal complex of the invention according to the embodiment immediately above, wherein M is Ir, $A^-$ is $BArF^-$; and n is 1.

In another embodiment, the invention relates to a metal complex of the invention according to the embodiment immediately above, wherein $L^1$ and $L^2$ together represent a diolefin selected from norbornadiene and cyclooctadiene and the nitrogen-phosphine ligand is of formula:

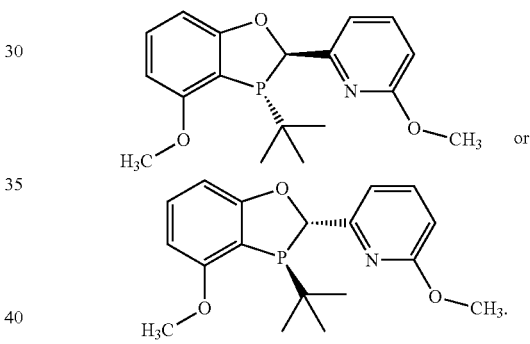

In another embodiment, the invention relates to a metal complex of the invention according to the embodiment immediately above, wherein $L^1$ and $L^2$ together represent cyclooctadiene and the nitrogen-phosphine ligand is of formula:

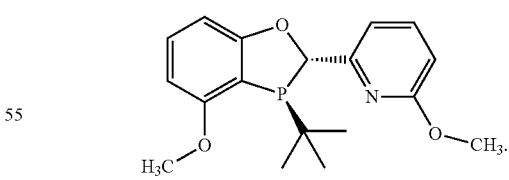

Asymmetric Hydrogenation

In one embodiment, the invention relates to a process for the asymmetric hydrogenation of a compound having a carbon-carbon or carbon-heteroatom double bond ("the asymmetric hydrogenation process of the invention"), the process comprising allowing said compound having a carbon-carbon or carbon-heteroatom double bond to react with hydrogen in the presence of a catalytic amount of the metal complex of the invention described in any of the embodiments above. Non-limiting examples of carbon-heteroatom double bonds include those formed between carbon and nitrogen, oxygen, or sulfur. In a preferred embodiment, carbon-heteroatom double bond is formed between carbon and nitrogen or carbon and oxygen.

In another embodiment, the invention relates to the asymmetric hydrogenation process of the invention in the embodiment described immediately above, wherein $L^1$ and $L^2$ together represent norbornadiene.

In another embodiment, the invention relates to the asymmetric hydrogenation process of the invention in the broadest embodiment described above, wherein $L^1$ and $L^2$ together represent octadiene.

In another embodiment, the invention relates to the asymmetric hydrogenation process of the invention in any of the embodiments described above, wherein M is Ir, $A^-$ is $BArF^-$, and n is 1.

Unless stated otherwise, the term "compounds of the invention" refers to the phosphine ligands of the invention (including bis-phosphine ligands of the invention) and the metal complexes of the invention.

For all compounds of the invention disclosed hereinabove in this application, in the event the nomenclature is in conflict with the structure, it shall be understood that the compound is defined by the structure.

Compounds of the invention also include their isotopically-labelled forms. An isotopically-labelled form of a compound of the present invention is identical to said compound of the invention but for the fact that one or more atoms of said compound of the invention have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. A compound of the present invention which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$(C_1-C_6)$alkoxy" or "$O(C_1-C_6)$alkyl" is a $(C_1-C_6)$alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$(C_1-C_6)$alkyl radical, unless otherwise specified, shall be understood to include —S(O)—$(C_1-C_6)$alkyl and —$S(O)_2$—$(C_1-C_6)$alkyl.

The term "$(C_3-C_{10})$carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_3-C_{10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl(decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$(C_6-C_{14})$aryl" refers to aromatic hydrocarbon rings containing from six to fourteen carbon ring atoms. The term $C_6-C_{14}$ aryl includes monocyclic rings, bicyclic rings and tricyclic rings where at least one of the rings is aromatic. Non-limiting examples of $C_{6-14}$ aryls include phenyl, indanyl, indenyl, benzocyclobutanyl, dihydronaphthyl, tetrahydronaphthyl, naphthyl, anthracenyl, benzocycloheptanyl and benzocycloheptenyl.

The term "(5 to 11-membered)heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen, phosphorus and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ⁶-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of non-aromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "(5 to 11-membered)heteroaryl" refers to an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O, P and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the $(C_{3-10})$carbocyclic rings, the (5 to 11-membered)heterocyclic rings, the nonaromatic portion of the bicyclic aryl rings, and the nonaromatic portion of the bicyclic heteroaryl rings can independently be replaced with a carbonyl, thiocarbonyl, or iminyl moiety.

The term "heteroatom" as used herein shall be understood to mean atoms other than carbon such as O, N, P and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The term "olefin" as used herein refers to an unsaturated hydrocarbon containing carbon atoms linked by a double bond (i.e., an alkene) such as, for example, ethylene, propene, 1-butene, 2-butene, styrene, norbornadiene, or cyclooctadiene. The term "diolefin" refers an unsaturated hydrocarbon containing two pairs of carbon atoms linked by double bonds, e.g., norbornadiene, or cyclooctadiene.

The compounds of the invention may be made using the general synthetic methods described below, which also constitute part of the invention.

General Synthetic Methods

The invention also provides processes for making compounds of formula Ia, Ib, IIa and IIb. In all methods, unless specified otherwise, $R^1$, $R^2$, $R^3$, $R^4$, $L^1$, $L^2$, A, M and n in the formulas below shall have the meaning of $R^1$, $R^2$, $R^3$, $R^4$, $L^1$, $L^2$, A, M and n in formula Ia, Ib, IIa and IIb of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Examples section. Typically, reaction progress may be monitored by thin layer chromatography (TLC), if desired, and intermediates and products may be purified by chromatography on silica gel and/or by recrystallization. The examples which follow are illustrative and, as recognized by one skilled in the art, particular reagents or conditions could be modified as needed for individual compounds without undue experimentation.

Starting materials and reagents are either commercially available or may be prepared by one skilled in the art using methods described in the chemical literature. Initial products of formula Ia, Ib, IIa and IIb may be modified further by methods known in the art to produce additional compounds of formula Ia, Ib, IIa and IIb.

Compounds of formula Ia, Ib wherein X is O, may be prepared as shown in Scheme 1.

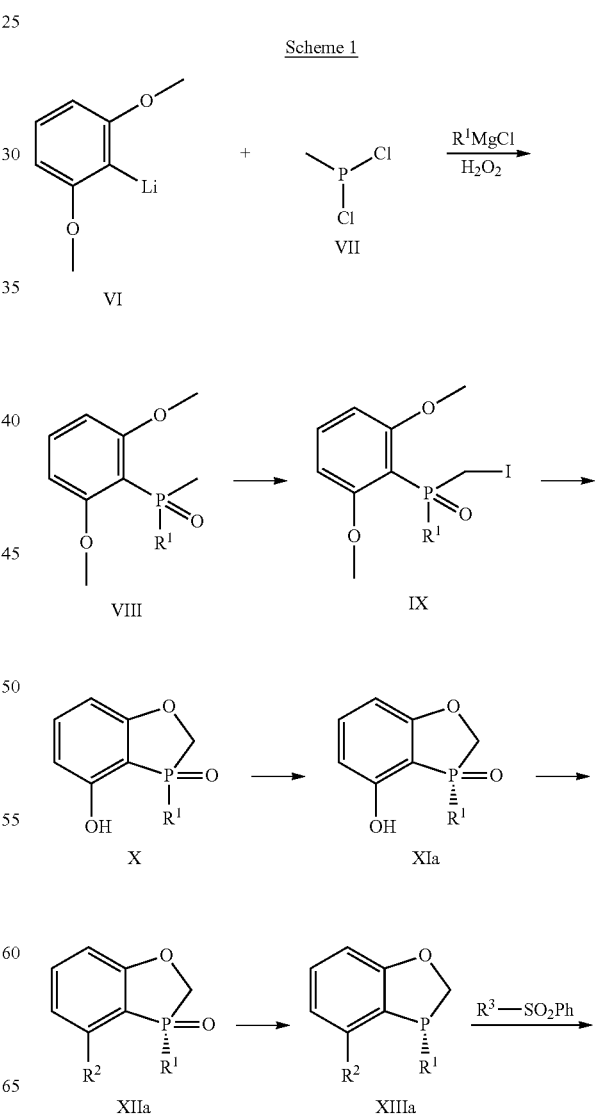

Scheme 2

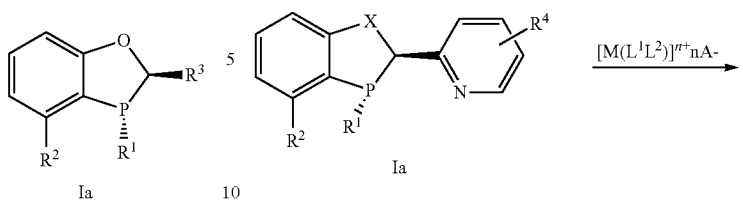

As illustrated in Scheme 1, reaction of dimethoxy phenyllithium VI with a dichlorophosphine of formula VII, in a suitable solvent, in the presence of an alkyl magnesium chloride and hydrogen peroxide provides a phosphine oxide of formula VIII. Iodination of the phosphine oxide VIII, in a suitable solvent, in the presence of a suitable base, provides the iodinated intermediate of formula IX. Demethylation of the methoxy groups of compound IX by a reagent such as boron tribromide (BBr$_3$) followed by cyclization, provides the corresponding cyclized intermediate of formula X. Resolution of the intermediate X using a resolving agent such as (−) menthyl chloroformate provides the corresponding (S) isomer of formula XIa. The hydroxyl group of compound XIa may be modified to other groups, such as methoxy, aryl etc., under standard reaction conditions known in the literature, to provide a compound of formula XIIa. The synthesis of compound XIIa is described in WO 2011/056737.

Alternately, resolution of the intermediate using a resolving agent such as (+) menthyl chloroformate provides the corresponding (R) isomer XXIb which may be converted to compounds of formula Ib by the method described in Scheme 1.

Reduction of the phosphine oxide in Compound XIIa, under suitable conditions provides Compound XIIIa Compound XIIIa may be further converted to a compound of formula Ia by the reaction with a heteroaryl sulfone, R$^3$SO$_2$Ph, in a suitable solvent in the presence of a suitable base to provide a compound of formula Ia.

Compounds of formula IIa and IIb may be prepared according to Scheme 2

As illustrated in Scheme 2, reaction of a compound of formula Ia with a transition metal salt [M(L$^1$L$^2$)]$^{n+}$nA$^−$, in a suitable solvent, provides a compound of formula IIa. Similarly, starting with a compound of formula Ib provides the corresponding compound of formula IIb.

In another embodiment, the invention relates to the asymmetric hydrogenation of prochiral molecules containing carbon-carbon or carbon-nitrogen double bonds, under suitable conditions, in the presence of the catalysts of the invention, to provide intermediates useful in the synthesis of pharmaceutically active compounds.

All of the compounds of the invention may prepared by the methods described above and in the Examples section below.

Examples

Synthesis of Compounds of Formula Ia and Ib (Compounds of formula Ia)

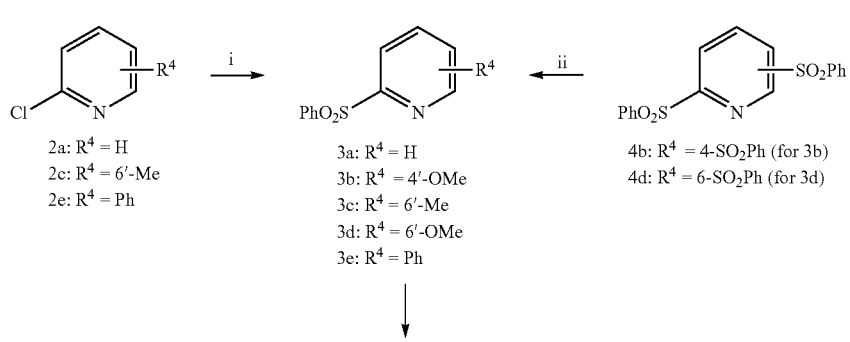

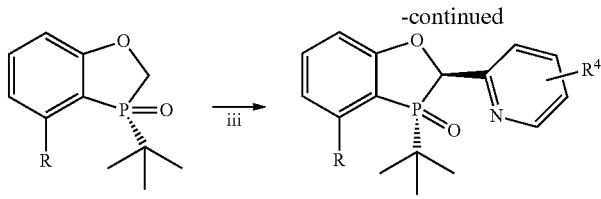 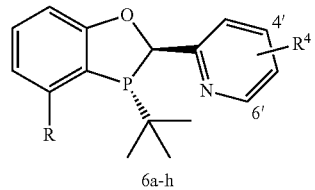

1a: R = OMe
1b: R = Ph
1c: R = 2,6-(MeO)₂Ph
1d: R = anthracene i. PhSO₂Na (1.5 equiv), in aq HOAc at 90° C. for 14 h;
ii. NaOMe ((1.1 equiv), THF, RT;
iii. LDA (3.0 equiv), −78° C. in THF, 2 h;
iv. PMHS (2 equiv), Ti(OiPr)₄ (2 equiv), THF, 65° C., 14 h.

i. PhSO₂Na (1.5 equiv), in aq HOAc at 90° C. for 14 h; ii. NaOMe ((1.1 equiv), THF, RT; iii. LDA (3.0 equiv), −78° C. in THF, 2 h; iv. PMHS (2 equiv), Ti(OiPr)₄ (2 equiv), THF, 65° C., 14 h.

Procedure for the Synthesis of the Sulphonylated Pyridines

2-Chloropyridine 2a (1.135 g, 10.0 mmol) is added to 5 mL of HOAc under an argon atmosphere. Phenyl sulfinic sodium salt (2.477 g, 15.0 mmol) is then added. The resulting reaction mixture is stirred at 95° C. for 24 h. After the completion of the reaction, the mixture is cooled down, water is added (10 ml) and the mixture is extracted with MeTHF (50 ml). The organic layer is washed with NaHCO₃ solution (10 ml) once and concentrated. 3a is purified on silica gel and eluted with 50% hexanes/EtOAc to yield 2.0 g (90% yield) of white solid after removing the solvent. ¹H NMR (400 MHz, CDCl₃) δ 8.67 (d, J=4.8 Hz, 1H), 8.21 (d, J=7.9 Hz, 1H), 8.08 (m, 2H), 7.95 (dt, J=7.8, 1.7 Hz, 1H), 7.60 (m, 1H), 7.55 (m, 2H), 7.48 (ddd, J=7.6, 4.7, 1.0 Hz, 1H); ¹³C NMR (100 MHz, CDCl₃) δ 158.8, 150.5, 138.9, 138.1, 133.8, 129.1, 128.9, 126.9, 122.2.

2,6-Bis(phenylsulfonyl)pyridine (4d)

To a N₂ purged reactor is charged 10.0 g (67.57 mmol) of 2,6-dichloropyridine, 16.64 g (101.4 mmol) of sodium benzenesulfinate, 5.6 g (20.73 mmol) of tetrabutylammonium chloride and 100 mL of N,N-dimethylacetamide. The mixture is heated to 100° C. and stirred for 4 h. Then another portion of 16.64 g (101.4 mmol) sodium benzenesulfinate is charged and the reactor contents is stirred at 100° C. for 14 h until more than 95% conversion is obtained. The mixture is cooled down to room temperature and 300 mL of water is added to observe formation of white precipitates. The slurry is stirred at room temperature for 1 h. The solid is filtered, washed with 20 ml of isopropanol, and dried under vacuum at 50° C. to provide 21.6 g of 2 as a white solid, 89% yield; mp 178.1-180.4° C. ¹H NMR (400 MHz, CDCl₃) δ 8.31 (d, J=7.6 Hz, 2H), 8.18-8.16 (m, 1H), 7.94-7.91 (m, 4H), 7.66 (tt, J=7.5, 1.2 Hz, 2H), 7.51 (t, J=7.8 Hz, 4H); ¹³C NMR (100 MHz, CDCl₃) δ 159.5, 140.6, 137.4, 134.2, 129.4, 129.1, 124.2; HRMS (ESI) m/z 360.0358 (M+H⁺), calc. for C₁₇H₁₄NO₄S₂ 360.0359.

2-Methoxy-6-(phenylsulfonyl)pyridine (3d)

To a N₂ purged reactor is charged 5.0 g (13.9 mmol) of 4d and 50 mL of anhydrous THF. The resulting slurry is treated drop-wise with MeONa (25 wt % in MeOH) (1.1 equiv). The resulting slurry is stirred for 1 h at room temperature, and a complete conversion is observed by LC-MS. The slurry is filtered, washed with IPA; and dried in oven overnight at 50° C. to give 1.94 g 3d as a white solid. The mother liquor is concentrated, 15 mL of IPA is added, and the mixture warmed until complete dissolution. The mixture is cooled down to 10° C. and held for 1 h. A second crop of solid is collected by filtration, and dried to yield another 1.17 g of white solid 3d, total 90% yield; mp 74.6-75.8° C. ¹H NMR (400 MHz, CDCl₃) δ 8.12-8.09 (m, 2H), 7.78-7.73 (m, 2H), 7.64 (tt, J=7.4, 1.3 Hz, 1H), 7.58-7.53 (m, 2H), 6.88 (dd, J=7.7, 1.4 Hz, 1H), 3.87 (s, 3H); ¹³C NMR (100 MHz, CDCl₃) δ 164.0, 155.7, 139.7, 138.9, 133.6, 129.1, 128.9, 115.5, 114.9, 54.0; HRMS (ESI) m/z 250.0528 (M+H⁺), calc. for C₁₂H₁₂NO₃S 250.0532.

2-Phenyl-6-(phenylsulfonyl)pyridine (3e)

To a stirred solution of bis-(phenylsulfonyl)pyridine 4d (1.0 g, 2.78 mmol) in 10 mL THF at room temperature is charged 1.0 M PhMgBr (5.56 ml, 2.0 equiv) slowly over a period of 10 min. The progress of the reaction is monitored by LC-MS. Upon complete consumption of the starting material (about 2 h), the mixture is quenched with MeOH (2 mL). The crude mixture is then evaporated to dryness, and the product is isolated by flash column chromatography (silica gel, 15% ethyl acetate in hexanes) and dried to yield 656 mg of 3e as a white solid, 80% yield. ¹H NMR (400 MHz, CDCl₃) δ 8.14-8.08 (m, 3H), 7.95-7.91 (m, 3H), 7.83-7.86 (m, 1H), 7.62-7.51 (m, 3H), 7.46-7.40 (m, 3H); ¹³C NMR (100 MHz, CDCl₃) δ 158.7, 158.0, 138.9, 138.7, 137.1, 133.7, 130.0, 129.2, 128.9, 128.8, 127.0, 123.1, 119.8.

Procedure for the Synthesis of the Phosphine Oxides (2R,3S)-3-(tert-butyl)-4-methoxy-2-(pyridin-2-yl)-2H-benzo[d][1,3]oxaphosphole 3-oxide (5a)

Intermediate 1a (1.0 g, 4.163 mmol) and pyridine sulfone 3a (0.913 g, 4.163 mmol) are dissolved in 10 ml of anhydrous THF under argon. The mixture is cooled to −78° C. with a dry ice/acetone bath. The stirred solution is treated with drop-wise with 2.64 mL (12.5 mmol) of LDA (2.0 M in THF/ethylbenzene). The internal temperature is maintained under −70° C. for an additional hour. Upon completion, the reaction is quenched with MeOH at −78° C. The mixture is warmed to room temperature and stirred for an additional 2 h. The reaction mixture should be basic at PH≥12. Aqueous NaOH (30 wt %) is added if necessary. The mixture is then concentrated down to a minimal volume. Water and CH₂Cl₂ is added to dilute the mixture. The organic layer is further extracted with $CH_2Cl_2$ and dried with anhydrous $Na_2SO_4$. The $CH_2Cl_2$ solution is concentrated and compound 5a is purified on silica gel with 5% MeOH in $CH_2Cl_2$ to yield 1.2 g of white solid after dryness, 91% yield; mp 186.1-188.5° C. $^1$H NMR (400 MHz, $CDCl_3$) δ 8.58 (d, J=4.7 Hz, 1H), 7.68 (dt, J=7.7, 1.7 Hz, 1H), 7.45 (t, J=8.3 Hz, 1H), 7.40 (dd, J=8.0, 0.5 Hz, 1H), 7.21 (t, J=6.2 Hz, 1H), 6.68 (dd, J=8.3, 3.0 Hz, 1H), 6.53 (dd, J=8.3, 4.2 Hz, 1H), 5.67 (d, $J_{H-P}$=2.9 Hz, 1H), 3.88 (s, 3H), 1.39 (d, $J_{H-P}$=16.6 Hz, 9H); $^{13}$C NMR (100 MHz, $CDCl_3$) δ 165.6 (d, $J_{C-P}$=15.0 Hz), 161.5 (d, $J_{C-P}$=1.9 Hz), 154.4 (d, $J_{C-P}$=3.4 Hz), 149.2, 136.7, 136.6, 123.0 (d, $J_{C-P}$=1.8 Hz), 122.3 (d, $J_{C-P}$=2.2 Hz), 106.1 (d, $J_{C-P}$=5.1 Hz), 103.6 (d, $J_{C-P}$=5.5 Hz), 103.2 (d, $J_{C-P}$=89.2 Hz), 79.1 (d, $J_{C-P}$=53.9 Hz), 55.6, 34.3 (d, $J_{C-P}$=73.9 Hz), 25.0; $^{31}$P NMR (160 MHz, $CDCl_3$) δ 61.65; HRMS (ESI) m/z 318.1237 (M+H$^+$), calc. for $C_{17}H_{21}NO_3P$ 318.1254.

(2R,3S)-3-(tert-butyl)-4-phenyl-2-(pyridin-2-yl)-2H-benzo[d][1,3]oxaphosphole 3-oxide (5b)

Compound 5b (1.09) g is isolated as a white solid after purification with 0-2% MeOH in $CH_2Cl_2$, 72% yield; mp 99.2-101.6° C. $^1$H NMR (400 MHz, $CDCl_3$) δ 8.62 (d, J=5.0 Hz, 1H), 7.76-7.73 (m, 3H), 7.57 (dt, J=7.9, 0.9 Hz, 1H), 7.48 (dd, J=8.0, 0.9 Hz, 1H), 7.18-7.34 (m, 3H), 7.26-7.22 (m, 1H), 7.13-7.07 (m, 2H), 5.71 (d, J=1.0 Hz, 1H), 0.91 (d, $J_{H-P}$=16.5 Hz, 9H); $^{13}$C NMR (100 MHz, $CDCl_3$) δ 164.6 (d, $J_{C-P}$=17.6 Hz), 154.8 (d, $J_{C-P}$=3.7 Hz), 149.3 (d, $J_{C-P}$=1.2 Hz), 147.0 (d, $J_{C-P}$=5.6 Hz), 140.6 (d, $J_{C-P}$=1.8 Hz), 136.7 (d, $J_{C-P}$=1.8 Hz), 134.9 (d, $J_{C-P}$=1.9 Hz), 129.9, 128.5, 128.4, 123.9 (d, $J_{C-P}$=7.8 Hz), 122.9 (d, $J_{C-P}$=1.8 Hz), 121.6 (d, $J_{C-P}$=2.2 Hz), 112.8 (d, $J_{C-P}$=85.9 Hz), 112.4 (d, $J_{C-P}$=5.3 Hz), 77.8 (d, $J_{C-P}$=55.6 Hz), 34.6 (d, $J_{C-P}$=71.3 Hz), 24.4; $^{31}$P NMR (160 MHz, $CDCl_3$) δ 62.19; HRMS (ESI) m/z 364.1459 (M+H$^+$), calc. for $C_{22}H_{23}NO_2P$ 364.1461.

(2R,3S)-3-(tert-butyl)-4-(2,6-dimethoxyphenyl)-2-(pyridin-2-yl)-2H-benzo[d][1,3]oxaphosphole 3-oxide (5c)

Compound 5c (1.37 g) is isolated as a white solid after purification with 100% EtOAc, 78% yield; mp 186.0-188.4° C. $^1$H NMR (500 MHz, $CDCl_3$) δ 8.57 (d, J=4.7 Hz, 1H), 7.68 (dt, J=7.8, 1.6 Hz, 1H), 7.56 (t, J=7.8 Hz, 1H), 7.47 (d, J=7.8 Hz, 1H), 7.27 (t, J=8.3 Hz, 1H), 7.21 (t, J=6.2 Hz, 1H), 7.05 (dd, J=8.2, 3.2 Hz, 1H), 6.98 (dd, J=7.4, 3.2 Hz, 1H), 6.58 (dd, J=8.2, 5.0 Hz, 2H), 5.60 (d, J=1.6 Hz, 1H), 3.74 (s, 3H), 3.58 (s, 3H), 0.95 (d, $J_{H-P}$=16.2 Hz, 9H); $^{13}$C NMR (125 MHz, $CDCl_3$) δ 164.2 (d, $J_{C-P}$=17.7 Hz), 158.8, 157.3, 154.9 (d, $J_{C-P}$=3.1 Hz), 149.1 (d, $J_{C-P}$=0.9 Hz), 138.8 (d, $J_{C-P}$=5.3 Hz), 136.4, 134.3, 129.9, 125.6 (d, $J_{C-P}$=8.4 Hz), 122.9 (d, $J_{C-P}$=1.4 Hz), 122.4 (d, $J_{C-P}$=2.3 Hz), 117.4 (d, $J_{C-P}$=2.0 Hz), 114.7 (d, $J_{C-P}$=89.5 Hz), 112.3 (d, $J_{C-P}$=5.4 Hz), 104.6, 103.0, 78.2 (d, $J_{C-P}$=55.3 Hz), 56.1, 55.4, 34.2 (d, $J_{C-P}$=71.8 Hz), 23.9 (d, $J_{C-P}$=0.7 Hz); $^{31}$P NMR (200 MHz, $CDCl_3$) δ 60.11; HRMS (ESI) m/z 424.1654 (M+H$^+$), calc. for $C_{24}H_{27}NO_4P$ 424.1672.

(2R,3S)-4-(anthracen-9-yl)-3-(tert-butyl)-2-(pyridin-2-yl)-2H-benzo[d][1,3]oxaphosphole 3-oxide (5d)

Compound 5d (1.73) g is isolated as a white solid after purification with 0-2% MeOH in $CH_2Cl_2$, 90% yield; mp 243-246° C. (decomp). $^1$H NMR (400 MHz, $CDCl_3$) δ 8.53 (d, J=5.0 Hz, 1H), 8.51 (s, 1H), 8.05 (d, J=8.4 Hz, 1H), 7.95 (d, J=8.4 Hz, 1H), 7.76-7.69 (m, 3H), 7.62 (t, J=8.6 Hz, 2H), 7.47-7.36 (m, 4H), 7.30 (dd, J=8.4, 2.6 Hz, 1H), 7.22 (d, J=6.0 Hz, 1H), 7.16 (dd, J=7.2, 3.2 Hz, 1H), 5.60 (d, J=4.4 Hz, 1H), 0.45 (d, $J_{H-P}$=16.5 Hz, 9H); $^{13}$C NMR (100 MHz, $CDCl_3$) δ 164.9 (d, $J_{C-P}$=16.2 Hz), 154.3 (d, $J_{C-P}$=3.2 Hz), 148.9, 142.1 (d, $J_{C-P}$=5.6 Hz), 136.6 (d, $J_{C-P}$=1.4 Hz), 134.5 (d, $J_{C-P}$=1.5 Hz), 134.4 (d, $J_{C-P}$=1.9 Hz), 131.3, 131.1, 130.3 (d, $J_{C-P}$=4.5 Hz), 128.7, 128.4, 127.8, 127.2, 126.5 (d, $J_{C-P}$=8.1 Hz), 126.2, 125.9, 125.7, 125.4, 124.8, 123.3 (d, $J_{C-P}$=2.2 Hz), 123.1 (d, $J_{C-P}$=1.5 Hz), 117.2 (d, $J_{C-P}$=85.5 Hz), 113.4 (d, $J_{C-P}$=4.9 Hz), 78.9 (d, $J_{C-P}$=55.7 Hz), 33.8 (d, $J_{C-P}$=71.3 Hz), 24.0; $^{31}$P NMR (160 MHz, $CDCl_3$) δ 58.55; HRMS (ESI) m/z 464.1770 (M+H$^+$), calc. for $C_{30}H_{27}NO_2P$ 464.1774.

(2R,3S)-3-(tert-butyl)-4-methoxy-2-(6-methoxypyridin-2-yl)-2H-benzo[d][1,3]oxaphosphole 3-oxide (5g)

Compound 5g (1.18 g) is isolated as a white solid after purification with 80% EtOAc in hexanes, 82% yield; mp 164.9-167.2° C. $^1$H NMR (400 MHz, $CDCl_3$) δ 7.56 (t, J=7.7 Hz, 1H), 7.44 (t, J=8.2 Hz, 1H), 6.98 (d, J=7.4 Hz, 1H), 6.69 (dd, J=8.4, 2.6 Hz, 1H), 6.64 (d, J=8.4 Hz, 1H), 6.51 (dd, J=8.0, 4.0 Hz, 1H), 5.55 (d, J=1.8 Hz, 1H), 3.89 (s, 3H), 3.87 (s, 3H), 1.41 (d, $J_{H-P}$=16.6 Hz, 9H); $^{13}$C NMR (100 MHz, $CDCl_3$) δ 165.6 (d, $J_{C-P}$=15.1 Hz), 163.4 (d, $J_{C-P}$=1.6 Hz), 161.6 (d, $J_{C-P}$=1.9 Hz), 151.8 (d, $J_{C-P}$=4.3 Hz), 139.1 (d, $J_{C-P}$=1.9 Hz), 136.5, 114.0 (d, $J_{C-P}$=3.0 Hz), 110.0 (d, $J_{C-P}$=2.2 Hz), 106.1 (d, $J_{C-P}$=5.2 Hz), 103.5 (d, $J_{C-P}$=5.6 Hz), 102.4 (d, $J_{C-P}$=89.2 Hz), 78.6 (d, $J_{C-P}$=53.9 Hz), 55.6, 53.4, 34.3 (d, $J_{C-P}$=74.3 Hz), 25.1; $^{31}$P NMR (160 MHz, $CDCl_3$) δ 61.51; HRMS (ESI) m/z 348.1350 (M+H$^+$), calc. for $C_{18}H_{23}NO_4P$ 348.1359.

(2R,3S)-3-(tert-butyl)-4-methoxy-2-(6-phenylpyridin-2-yl)-2H-benzo[d][1,3]oxaphosphole 3-oxide (5h)

Compound 5h (1.16 g) is isolated as a white solid after purification with 50% EtOAc in hexanes, 71% yield; mp 172.2-174.3° C. $^1$H NMR (400 MHz, $CDCl_3$) δ 7.99 (d, J=7.9 Hz, 2H), 7.75 (t, J=7.8 Hz, 1H), 7.66 (d, J=7.9 Hz, 1H), 7.48-7.35 (m, 5H), 6.71 (dd, J=8.2, 2.9 Hz, 1H), 6.54 (dd, J=8.1, 4.1 Hz, 1H) 5.77 (d, J=3.3 Hz, 1H), 3.88 (s, 3H), 1.45 (d, J=16.5 Hz, 9H); $^{13}$C NMR (100 MHz, $CDCl_3$) δ 165.7 (d, $J_{C-P}$=15.0 Hz), 161.5 (d, $J_{C-P}$=1.9 Hz), 156.6 (d, $J_{C-P}$=1.2 Hz), 154.2 (d, $J_{C-P}$=3.6 Hz), 139.2, 137.5 (d, $J_{C-P}$=1.7 Hz), 136.6, 128.9, 128.6, 127.0, 120.6 (d, $J_{C-P}$=2.4 Hz), 119.7 (d, $J_{C-P}$=1.9 Hz), 106.2 (d, $J_{C-P}$=5.1 Hz), 103.5 (d, $J_{C-P}$=5.6 Hz), 102.7 (d, $J_{C-P}$=89.0 Hz), 79.5 (d, $J_{C-P}$=53.2 Hz), 55.6, 34.3 (d, $J_{C-P}$=73.8 Hz), 25.2; $^{31}$P NMR (160 MHz, $CDCl_3$) δ 61.24; HRMS (ESI) m/z 394.1572 (M+H$^+$), calc. for $C_{23}H_{25}NO_3P$ 394.1567.

Procedure for the Phosphine Oxides Reduction:

To a Schlenk flask under argon, phosphine oxide 5a (500 mg, 1.576 mmol) is dissolved in 10 mL of THF. 1.0 mL of PMHS and 0.93 mL (3.152 mmol) of Ti(OiPr)$_4$ are added. The resulting mixture is stirred for 14 h at 65° C. under argon. The completion of the reaction is monitored by $^{31}$P NMR of aliquots of the mixture. Upon completion, degassed 30% aqueous NaOH (20 ml) is added slowly to the mixture and allowed to stir for 1 hr at 65° C. The mixture is then cooled down to room temperature, and THF is concentrated. The product is extracted with degassed tert-butyl methyl ether (3×30 mL) and the organic layer is filtered through a plug of neutral alumina and with anhydrous MgSO$_4$ on the top. 410 mg 6a (86% yield) is obtained as white solid after evaporation of the solvent under reduced pressure. $^1$H NMR (400 MHz, $CDCl_3$) δ 8.55 (d, J=4.7 Hz, 1H), 7.51 (td, J=7.7, 1.6 Hz, 1H), 7.28 (t, J=8.1 Hz, 1H), 7.10 (d, J=7.8 Hz, 1H), 7.06 (t, J=6.2 Hz, 1H), 6.72 (d, J=8.2 Hz, 1H), 6.47 (dd, J=8.1, 3.6 Hz, 1H), 6.02 (s, 1H), 3.78 (s, 3H), 1.11 (d, $J_{H-P}$=12.4 Hz, 9H); $^{13}$C NMR (100 MHz, CDCl$_3$) δ 165.6 (d, $J_{C-P}$=15.2 Hz), 161.5 (d, $J_{C-P}$=1.8 Hz), 154.4 (d, $J_{C-P}$=3.6 Hz), 149.2 (d, $J_{C-P}$=0.8 Hz), 136.7, 136.6, 123.0 (d, $J_{C-P}$=1.7 Hz), 122.2 (d, $J_{C-P}$=2.4 Hz), 106.1 (d, $J_{C-P}$=5.2 Hz), 103.6 (d, $J_{C-P}$=5.6 Hz), 103.2 (d, $J_{C-P}$=89.2 Hz), 79.1 (d, $J_{C-P}$=53.8 Hz), 55.6, 34.2 (d, $J_{C-P}$=73.7 Hz), 25.0; $^{31}$P NMR (160 MHz, CDCl$_3$) δ 12.85; HRMS (ESI) m/z 302.1319 (M+H$^+$), calc. for $C_{17}H_{24}NO_2P$ 302.1304.

2-((2R,3R)-3-(tert-butyl)-4-phenyl-2,3-dihydrobenzo[d][1,3]oxaphosphol-2-yl)pyridine (6b)

Compound 6b (383 mg) is isolated as a white solid, 70% yield. $^1$H NMR (500 MHz, CDCl$_3$) δ 8.63 (d, J=4.5 Hz, 1H), 7.59-7.62 (m, 3H), 7.42 (t, J=7.8 Hz, 1H), 7.25-7.35 (m, 4H), 7.14 (t, J=6.7 Hz, 1H), 7.08 (d, J=8.0 Hz, 1H), 7.05 (dd, J=7.4 Hz, 3.4 Hz, 1H), 6.03 (s, 1H), 0.79 (d, J=12.2 Hz, 9H); $^{13}$C NMR (125 MHz, CDCl$_3$) δ 164.4, 161.3 (d, $J_{C-P}$=14.3 Hz), 149.6 (d, $J_{C-P}$=1.7 Hz), 146.5 (d, $J_{C-P}$=12.9 Hz), 142.1, 136.7 (d, $J_{C-P}$=1.2 Hz), 131.6, 129.3, 129.1, 128.4, 127.4, 122.6 (d, $J_{C-P}$=2.8 Hz), 121.9 (d, $J_{C-P}$=2.5 Hz), 120.6 (d, $J_{C-P}$=22.3 Hz), 119.2 (d, $J_{C-P}$=3.5 Hz), 109.9, 85.3 (d, $J_{C-P}$=27.4 Hz), 32.8 (d, $J_{C-P}$=22.6 Hz), 26.8 (d, $J_{C-P}$=13.8 Hz); $^{31}$P NMR (200 MHz, CDCl$_3$) δ 15.38; HRMS (ESI) m/z 348.1512 (M+H$^+$), calc. for $C_{22}H_{23}NOP$ 348.1512.

2-((2R,3R)-3-(tert-butyl)-4-(2,6-dimethoxyphenyl)-2,3-dihydrobenzo[d][1,3]oxaphosphol-2-yl)pyridine (6c)

Compound 6c (407 mg) is isolated as a white solid, 75% yield. $^1$H NMR (400 MHz, CDCl$_3$) δ 8.58 (d, J=4.7 Hz, 1H), 7.58 (dt, J=8.0, 1.5 Hz, 1H), 7.42 (t, J=7.8 Hz, 1H), 7.26-7.21 (m, 2H), 7.12 (t, J=6.0 Hz, 1H), 7.05 (d, J=8.0 Hz, 1H), 6.93 (dd, J=7.6, 3.2 Hz, 1H), 6.57 (d, J=8.4 Hz, 1H), 6.51 (d, J=8.4 Hz, 1H), 5.99 (s, 1H), 3.73 (s, 3H), 3.26 (s, 3H), 0.88 (d, $J_{H-P}$=12.2 Hz, 9H); $^{13}$C NMR (100 MHz, CDCl$_3$) δ 163.6, 161.7 (d, $J_{C-P}$=14.2 Hz), 157.6, 156.9, 149.2 (d, $J_{C-P}$=1.5 Hz), 139.1 (d, $J_{C-P}$=17.0 Hz), 136.5, 130.9, 129.1, 124.4 (d, $J_{C-P}$=4.1 Hz), 123.9 (d, $J_{C-P}$=17.1 Hz), 121.6 (d, $J_{C-P}$=2.4 Hz), 119.5 (d, $J_{C-P}$=3.7 Hz), 119.3 (d, $J_{C-P}$=21.5 Hz), 109.3, 104.4, 103.5, 86.0 (d, $J_{C-P}$=28.1 Hz), 55.43, 55.41, 31.9 (d, $J_{C-P}$=21.1 Hz), 26.7 (d, $J_{C-P}$=14.7 Hz); $^{31}$P NMR (160 MHz, CDCl$_3$) δ 17.71; HRMS (ESI) m/z 408.1700 (M+H$^+$), calc. for $C_{24}H_{27}NO_3P$ 408.1723.

2-((2R,3R)-4-(anthracen-9-yl)-3-(tert-butyl)-2,3-dihydrobenzo[d][1,3]oxaphosphol-2-yl)pyridine (6d)

Compound 6d (613 mg) is isolated as white solid, 87% yield. $^1$H NMR (500 MHz, CDCl$_3$) δ 8.4-8.2 (m, 2H), 7.80-7.76 (m, 3H), 7.48-6.79 (m, 11H), 5.88 (s, 1H), 0.45 (d, $J_{H-P}$=11.5 Hz, 9H); $^{13}$C NMR (125 MHz, CDCl$_3$) δ 164.6, 161.2 (d, $J_{C-P}$=14.5 Hz), 149.7, 142.8 (d, $J_{C-P}$=16.6 Hz), 136.6, 136.0, 131.5, 131.3, 130.6, 128.9, 128.6, 128.3, 127.2, 127.0, 126.9, 125.8 (d, $J_{C-P}$=3.6 Hz), 125.6, 125.4, 125.3, 124.9, 124.8 (d, $J_{C-P}$=21.3 Hz), 121.9 (d, $J_{C-P}$=2.0 Hz), 119.3 (d, $J_{C-P}$=3.8 Hz), 110.4, 86.2 (d, $J_{C-P}$=27.6 Hz), 31.6 (d, $J_{C-P}$=22.4 Hz), 27.1 (d, $J_{C-P}$=14.6 Hz); $^{31}$P NMR (200 MHz, CDCl$_3$) δ 15.46; HRMS (ESI) m/z 448.1823 (M+H$^+$), calc. for $C_{30}H_{27}NOP$ 448.1825.

2-((2R,3R)-3-(tert-butyl)-4-methoxy-2,3-dihydrobenzo[d][1,3]oxaphosphol-2-yl)-6-methoxypyridine (6g)

Compound 6g (465 mg) is prepared as a white solid according to the same procedure as above with addition of 2.1 mL of PMHS, 89% yield. $^1$H NMR (500 MHz, CDCl$_3$) δ 7.41 (t, $J_{H-P}$=7.8 Hz, 1H), 7.29 (t, $J_{H-P}$=8.2 Hz, 1H), 6.74 (d, $J_{H-P}$=7.5 Hz, 1H), 6.70 (d, $J_{H-P}$=8.2 Hz, 1H), 6.52 (d, $J_{H-P}$=8.2 Hz, 1H), 6.48 (dd, $J_{H-P}$=8.2, 3.7 Hz, 1H), 5.92 (s, 1H), 3.88 (s, 3H), 3.79 (s, 3H), 1.13 (d, $J_{H-P}$=12.4 Hz, 9H); $^{13}$C NMR (125 MHz, CDCl$_3$) δ 165.4, 163.5 (d, $J_{C-P}$=1.9 Hz), 162.2 (d, $J_{C-P}$=11.8 Hz), 158.7 (d, $J_{C-P}$=14.6 Hz), 138.9 (d, $J_{C-P}$=1.2 Hz), 132.3, 111.1 (d, $J_{C-P}$=3.8 Hz), 109.6 (d, $J_{C-P}$=17.5 Hz), 108.7 (d, $J_{C-P}$=2.6 Hz), 104.2, 103.1 (d, $J_{C-P}$=1.9 Hz), 85.8 (d, $J_{C-P}$=27.0 Hz), 55.4, 53.1, 33.3 (d, $J_{C-P}$=22.4 Hz), 27.2 (d, $J_{C-P}$=14.3 Hz); $^{31}$P NMR (200 MHz, CDCl$_3$) δ 14.24; HRMS (ESI) m/z (M+H$^+$) 332.1401, calc. for $C_{18}H_{23}NO_3P$ 332.1410.

2-((2R,3R)-3-(tert-butyl)-4-methoxy-2,3-dihydrobenzo[d][1,3]oxaphosphol-2-yl)-6-phenylpyridine (6h)

Compound 6h (386 mg) is isolated as a white solid, 65% yield. $^1$H NMR (500 MHz, CDCl$_3$) δ 8.02-8.04 (m, 2H), 7.60 (t, J=7.8 Hz, 1H), 7.55-7.52 (m, 1H), 7.46-7.43 (m, 2H), 7.40-7.37 (m, 1H), 7.31 (t, J=8.1 Hz, 1H), 7.09 (d, J=7.7 Hz, 1H), 6.76 (d, J=8.1 Hz, 1H), 6.50 (dd, J=8.2, 3.6 Hz, 1H), 6.14 (s, 1H), 3.80 (s, 3H), 1.17 (d, J=12.4 Hz, 9H); $^{13}$C NMR (125 MHz, CDCl$_3$) δ 165.4, 162.2 (d, $J_{C-P}$=11.7 Hz), 161.2 (d, $J_{C-P}$=14.8 Hz), 156.5 (d, $J_{C-P}$=1.9 Hz), 139.2, 137.3 (d, $J_{C-P}$=1.2 Hz), 132.4, 128.9, 128.6, 126.9, 118.2 (d, $J_{C-P}$=2.6 Hz), 117.2 (d, $J_{C-P}$=3.5 Hz), 109.6 (d, $J_{C-P}$=17.7 Hz), 104.2, 103.2 (d, $J_{C-P}$=2.0 Hz), 86.3 (d, $J_{C-P}$=27.3 Hz), 55.4, 32.5 (d, $J_{C-P}$=22.4 Hz), 27.3 (d, $J_{C-P}$=14.2 Hz); $^{31}$P NMR (200 MHz, CDCl$_3$) δ 14.52; HRMS (ESI) m/z (M+H$^+$) 378.1600, calc. for $C_{23}H_{25}NO_2P$ 378.1617.

Synthesis of Compounds of Formula IIa and IIb

Procedure for the Synthesis of iridium complexes:

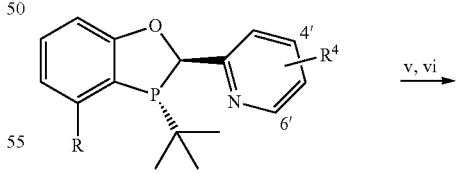

6a: R = OMe, R$^4$ = H
6b: R = Ph, R$^4$ = H
6c: R = 2,6-(MeO)$_2$Ph, R$^4$ = H
6d: R = anthracene, R$^4$ = H
6e: R = OMe, R$^4$ = 4'-OMe
6f: R = OMe, R$^4$ = 6'-Me
6g: R = OMe, R$^4$ = 6'-OMe
6h: R = OMe, R$^4$ = 6'-Ph (Compounds of formula Ia)

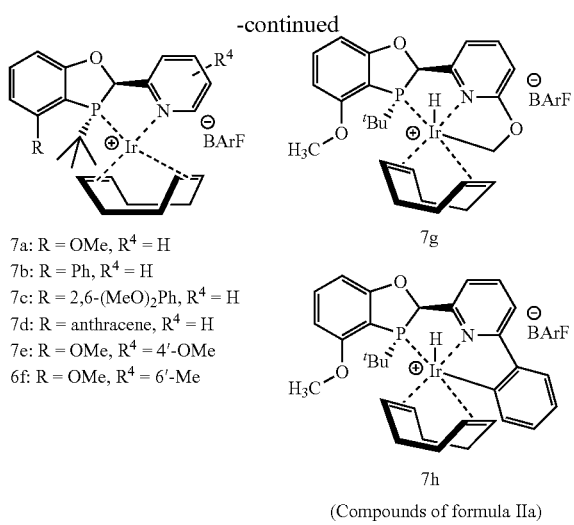

7a: R = OMe, R⁴ = H
7b: R = Ph, R⁴ = H
7c: R = 2,6-(MeO)₂Ph, R⁴ = H
7d: R = anthracene, R⁴ = H
7e: R = OMe, R⁴ = 4′-OMe
6f: R = OMe, R⁴ = 6′-Me (Compounds of formula IIa)

v. [Ir(COD)Cl]₂ (0.5 equiv), 40° C., 0.5 h;
vi. NaBArF (1.0 equiv), H₂O, RT, 1-12 h.

v. [Ir(COD)Cl]$_2$ (0.5 equiv), 40° C., 0.5 h; vi. NaBArF (1.0 equiv), H$_2$O, RT, 1-12 h.

{2-((2R,3R)-3-(tert-butyl)-4-methoxy-2,3-dihydrobenzo[d][1,3]oxaphosphol-2-yl)pyridine}(η⁴-1,5-cyclooctadiene)iridium (I) tetrakis[3,5-bis(trifluoromethyl)phenyl]borate (7a)

A solution of 6a (100 mg, 0.332 mmol) and [IrCl(COD)]$_2$ (115.0 mg, 0.166 mmol) in degassed CH$_2$Cl$_2$ (6 mL) is heated for 1 h at 45° C. under argon. After cooling to room temperature, NaBArF (318 mg, 0.348 mmol) is added followed immediately by 10 ml of degassed water. The two layers are stirred vigorously for 30 min. After separation of the layers, the aqueous layer is extracted twice with CH$_2$Cl$_2$ (2 mL). The combined organic layer is dried over Na$_2$SO$_4$ and concentrated to 1 mL. The mixture is then passed through a short plug of silica under argon using CH$_2$Cl$_2$ as eluent. The center of the first orange fraction is collected and dried to give 413 mg of 6a as a red-orange solid, 85% yield. $^1$H NMR (500 MHz, CD$_2$Cl$_2$) δ 8.09 (d, J=6.0 Hz, 1H), 8.05 (t, J=7.6 Hz, 1H), 7.98 (d, J=7.8 Hz, 1H), 7.63 (s, BArF), 7.47 (s, BArF), 7.42 (t, J=6.8 Hz, 1H), 7.32 (t, J=8.3 Hz, 1H), 6.52-6.55 (m, 2H), 5.96 (s, 1H), 5.25-5.28 (m, 1H), 5.05 (m, 1H), 4.83-4.88 (m, 1H), 4.41-4.43 (m, 1H), 3.84 (s, 3H), 2.61-2.65 (m, 1H), 2.30-2.42 (m, 2H), 2.22-2.28 (m, 2H), 2.01-2.07 (m, 1H), 1.72-1.86 (m, 2H), 1.15 (d, J$_{H-P}$=16.2 Hz, 9H); $^{13}$C NMR (125 MHz, CD$_2$Cl$_2$) δ 164.7 (d, J$_{C-P}$=10.0 Hz), 162.7 (d, J$_{C-P}$=4.1 Hz), 161.5 (q, $^1$J$_{C-B}$=50.2 Hz), 160.4 (d, J$_{C-P}$=5.5 Hz), 147.8, 140.6 (d, J$_{C-P}$=0.9 Hz), 135.3 (d, J$_{C-P}$=1.4 Hz), 134.0 (br), 128.2 (qq, $^2$J$_{C-F}$=31.4 Hz, $^4$J$_{C-F}$=2.8 Hz), 127.0, 126.4 (d, J$_{C-F}$=7.4 Hz), 125.7, 124.9 (q, $^1$J$_{C-F}$=272.3 Hz), 116.7 (sept, $^3$J$_{C-F}$=4.0 Hz), 105.2 (d, J$_{C-P}$=4.0 Hz), 104.4 (d, J$_{C-P}$=5.2 Hz), 94.6 (d, J$_{C-P}$=9.7 Hz), 93.4 (d, J$_{C-P}$=13.7 Hz), 84.8 (d, J$_{C-P}$=24.2 Hz), 63.9 (d, J$_{C-P}$=19.8 Hz), 55.1, 34.7 (d, J$_{C-P}$=4.5 Hz), 34.5 (d, J$_{C-P}$=22.1 Hz), 29.9 (d, J$_{C-P}$=1.9 Hz), 29.8 (d, J$_{C-P}$=1.9 Hz), 25.5 (d, J$_{C-P}$=2.4 Hz), 25.4 (d, J$_{C-P}$=4.5 Hz); $^{31}$P NMR (200 MHz, CD$_2$Cl$_2$) δ 47.33 (s); HRMS (ESI) m/z 602.1853 (M⁺), calc. for [IrC$_{25}$H$_{32}$NO$_2$P]⁺ 602.1795; 863.0658 (BArF), calc. for [C$_{32}$H$_{12}$BF$_{24}$]⁻ 863.0654.

{2-((2R,3R)-3-(tert-butyl)-4-phenyl-2,3-dihydrobenzo[d][1,3]oxaphosphol-2-yl)pyridine}(η⁴-1,5-cyclooctadiene)iridium (I) tetrakis[3,5-bis(trifluoromethyl)phenyl]borate (7b)

Compound 7b (375 mg) is isolated as a red-orange solid, 75% yield. $^1$H NMR (500 MHz, CDCl$_3$) δ 8.11 (d, J=6.0 Hz, 1H), 7.88-7.92 (m, 2H), 7.63 (s, BArF), 7.39-7.47 (m, 5H), 7.43 (s, BArF), 7.36 (t, J=7.8 Hz, 1H), 7.29 (dt, J=6.5, 2.0 Hz, 1H), 6.95 (d, J=8.3 Hz, 1H), 6.88 (dd, J=7.5, 4.0 Hz, 1H), 5.86 (s, 1H), 4.90 (m, 1H), 4.75 (m, 1H), 4.26 (m, 1H), 3.69 (m, 1H), 2.36-2.43 (m, 1H), 2.25-2.31 (m, 2H), 2.05-2.16 (m, 2H), 1.85-2.91 (m, 2H), 1.77-1.81 (m, 1H), 0.91 (d, J$_{H-P}$=15.9 Hz, 9H); $^{13}$C NMR (125 MHz, CDCl$_3$) δ 163.9 (d, J$_{C-P}$=9.7 Hz), 161.5 (d, J$_{C-P}$=4.7 Hz), 161.2 (q, $^1$J$_{C-B}$=50.2 Hz), 147.1, 145.4 (d, J$_{C-P}$=9.5 Hz), 140.1, 139.8 (d, J$_{C-P}$=1.8 Hz), 133.7 (br), 133.4 (d, J$_{C-P}$=1.8 Hz), 128.2, 128.0 (qq, $^2$J$_{C-F}$=31.6 Hz, $^4$J$_{CT}$=3.0 Hz), 127.8, 127.6, 125.7 (d, J$_{C-P}$=6.6 Hz), 125.5, 125.3 (d, J$_{C-P}$=7.0 Hz), 124.6 (q, $^1$J$_{C-F}$=272.8 Hz), 116.4 (sept, $^3$J$_{C-P}$=4.0 Hz), 113.1 (d, J$_{C-P}$=38.2 Hz), 111.5 (d, J$_{C-P}$=3.8 Hz), 93.0 (d, J$_{C-P}$=14.3 Hz), 92.6 (d, J$_{C-P}$=9.1 Hz), 83.0 (d, J$_{C-P}$=24.5 Hz), 67.1, 63.1, 34.1 (d, J$_{C-P}$=19.9 Hz), 33.4 (d, J$_{C-P}$=4.6 Hz), 30.4 (d, J$_{C-P}$=2.2 Hz), 28.8 (d, J$_{C-P}$=1.7 Hz), 26.3 (d, J$_{C-P}$=2.7 Hz), 25.5 (d, J$_{C-P}$=4.1 Hz); $^{31}$P NMR (200 MHz, CDCl$_3$) δ 47.12 (s); HRMS (ESI) m/z 648.2047 (M⁺), calc. for [IrC$_{30}$H$_{34}$NOP]⁺ 648.2002; 863.0632 (BArF), calc. for [C$_{32}$H$_{12}$BF$_{24}$]⁻ 863.0654.

{2-((2R,3R)-3-(tert-butyl)-4-(2,6-dimethoxyphenyl)-2,3-dihydrobenzo[d][1,3]oxaphosphol-2-yl)pyridine}(η⁴-1,5-cyclooctadiene)iridium (I) tetrakis[3,5-bis(trifluoromethyl)phenyl]borate (7c)

Compound 7c (418 mg) is isolated as a red-orange solid, 86% yield. $^1$H NMR (500 MHz, CD$_2$Cl$_2$) δ 8.19 (d, J=6.0 Hz, 1H), 7.98-8.03 (m, 2H), 7.64 (s, BArF), 7.47 (s, BArF), 7.41 (dt, J=6.9, 1.8 Hz, 1H), 7.31-7.35 (m, 2H), 6.95 (d, J=8.0 Hz, 1H), 6.75 (d, J=8.4 Hz, 1H), 7.72 (dd, J=7.6, 3.9 Hz, 1H), 6.62 (d, J=8.4 Hz, 1H), 5.93 (s, 1H), 4.77-4.83 (m, 1H), 4.37-4.40 (m, 1H), 4.19-4.20 (m, 1H), 3.60-3.65 (m, 1H), 3.62 (s, 3H), 3.55 (s, 3H), 2.38-2.45 (m, 2H), 1.89-2.22 (m, 4H), 1.48-1.56 (m, 2H), 1.06 (d, J$_{H-P}$=15.8 Hz, 9H); $^{13}$C NMR (125 MHz, CD$_2$Cl$_2$) δ 165.4 (d, J$_{C-P}$=9.5 Hz), 162.8 (d, J$_{C-P}$=4.5 Hz), 162.3 (q, $^1$J$_{C-B}$=50.4 Hz), 157.8 (d, J$_{C-P}$=25.7 Hz), 148.4, 141.4, 139.8 (d, J$_{C-P}$=10.3 Hz), 135.1 (br), 134.2 (d, J$_{C-P}$=1.8 Hz), 130.7, 129.4 (qq, J$_{C-F}$=31.6 Hz, $^4$J$_{CT}$=2.9 Hz), 127.2 (d, J$_{C-P}$=1.7 Hz), 127.1, 126.8, 126.0 (q, $^1$J$_{C-F}$=272.7 Hz), 118.2, 117.8 (sept, $^3$J$_{C-F}$=4.2 Hz), 112.1 (d, J$_{C-P}$=3.9 Hz), 104.6 (d, J$_{C-P}$=17.4 Hz), 93.4 (d, J$_{C-P}$=7.7 Hz), 89.6 (d, J$_{C-P}$=16.8 Hz), 84.5 (d, J$_{C-P}$=24.8 Hz), 67.6, 65.3, 56.3, 55.7, 36.9 (d, J$_{C-P}$=5.5 Hz), 34.8 (d, J$_{C-P}$=20.6 Hz), 32.9, 29.9, 26.3 (d, J$_{C-P}$=4.1 Hz), 25.6 (d, J$_{C-P}$=2.9 Hz); $^{31}$P NMR (200 MHz, CD$_2$Cl$_2$) δ 50.30 (s); HRMS (ESI) m/z 708.2173 (M⁺), calc. for [IrC$_{32}$H$_{38}$NO$_3$P]⁺ 708.2213; 863.0680 (BArF), calc. for [C$_{32}$H$_{12}$BF$_{24}$]⁻ 863.0654.

{2-((2R,3R)-4-(anthracen-9-yl)-3-(tert-butyl)-2,3-dihydrobenzo[d][1,3]oxaphosphol-2-yl)pyridine}(η⁴-1,5-cyclooctadiene)iridium (I) tetrakis[3,5-bis(trifluoromethyl)phenyl]borate (7d)

Compound 7d (427 mg) is isolated as a red-orange solid, 82% yield. $^1$H NMR (500 MHz, CDCl$_3$) δ 8.56 (s, 1H), 8.16 (d, J=8.3 Hz, 1H), 8.12 (d, J=5.2 Hz, 1H), 8.03 (d, J=8.2 Hz, 1H), 7.89-7.95 (m, 2H), 7.63 (s, BArF), 7.59 (d, J=8.7 Hz, 2H), 7.37-7.51 (m, 4H), 7.44 (s, BArF), 7.13 (d, J=8.2 Hz, 1H), 7.08 (t, J=7.2 Hz, 1H), 6.88 (d, J=6.3 Hz, 1H), 6.73 (d, J=8.2 Hz, 1H), 5.94 (s, 1H), 4.46-4.52 (m, 1H), 3.99-4.05 (m, 1H), 3.68-3.75 (m, 1H), 2.35-2.41 (m, 1H), 1.89-1.95 (m, 1H), 1.68-1.81 (m, 3H), 1.49-1.56 (m, 1H), 1.07-1.17 (m, 2H), 0.88 (d, J=15.9 Hz, 9H); $^{13}$C NMR (125 MHz, CDCl$_3$) δ 163.5 (d, $J_{C-P}$=9.5 Hz), 161.5 (d, $J_{C-P}$=4.5 Hz), 160.1 (q, $^1J_{C-B}$=49.8 Hz), 147.2, 141.7 (d, $J_{C-P}$=10.2 Hz), 140.1, 133.7 (br), 132.1, 130.6 (d, $J_{C-P}$=32.2 Hz), 129.3, 128.9, 128.8, 128.0, 127.9 (qq, $^2J_{C-F}$=31.4 Hz, $^4J_{C-F}$=3.0 Hz), 127.5, 127.2 (d, $J_{C-P}$=7.1 Hz), 126.7, 125.9, 125.7 (d, $J_{C-P}$=6.6 Hz), 125.6, 125.2 (d, $J_{C-P}$=5.1 Hz), 124.9 (d, $J_{C-P}$=11.6 Hz), 124.6 (q, $^1J_{C-F}$=273.0 Hz), 124.2, 117.6 (d, $J_{C-P}$=37.5 Hz), 116.5 (sept, $^3J_{C-F}$=4.0 Hz), 112.0 (d, $J_{C-P}$=3.7 Hz), 92.1 (d, $J_{C-P}$=7.6 Hz, COD, CH), 89.6 (d, $J_{C-P}$=16.2 Hz, COD, CH), 83.6 (d, $J_{C-P}$=24.9 Hz), 65.2 (COD, CH), 62.1 (COD, CH), 33.4 (d, $J_{C-P}$=5.2 Hz, COD, CH$_2$), 33.2 (d, $J_{C-P}$=20.2 Hz), 31.0 (COD, CH$_2$), 28.2 (COD, CH$_2$), 25.5 (d, $J_{C-P}$=4.1 Hz), 23.6 (d, $J_{C-P}$=3.0 Hz, COD, CH$_2$); $^{31}$P NMR (200 MHz, CDCl$_3$) δ 47.67 (s); HRMS (ESI) m/z 748.2315 (M$^+$), calc. for [IrC$_{31}$H$_{36}$NO$_2$P]$^+$ 748.2313; 863.0654 (BArF), calc. for [C$_{32}$H$_{12}$BF$_{24}$]$^-$ 863.0654.

Complex 7g

After addition of NaBArF, the mixture is stirred at room temperature for 12 h until $^{31}$P NMR indicates complete conversion. Compound 7g (431 mg) is isolated as a light yellow solid (87% yield) after the same work up as above. $^1$H NMR (500 MHz, CDCl$_3$) δ 7.69 (s, BArF), 7.64 (t, J=8.1 Hz, 1H), 7.49 (s, BArF), 7.45 (t, J=8.5 Hz, 1H), 7.32 (dd, $^3J_{H-P}$=7.1 Hz, J=5.1 Hz, 1H, OCH$_2$), 7.23 (d, J=7.1 Hz, 1H), 6.89 (dd, J=8.7, 1.0 Hz, 1H), 6.72 (m, 1H, OCH$_2$), 6.69 (t, J=4.0 Hz, 1H), 6.66 (dd, J=8.4, 1.8 Hz, 1H), 6.50 (d, J=6.3 Hz, 1H), 4.37-4.39 (m, 1H), 4.29-4.31 (m, 2H), 3.96 (s, 3H), 3.87-3.90 (m, 1H), 2.57-2.62 (m, 2H), 2.18-2.32 (m, 2H), 1.95-2.01 (m, 1H), 1.71-1.75 (m, 1H), 1.51-1.53 (m, 1H), 1.21 (d, J=17.0 Hz, 9H), 0.83-0.93 (m, 1H), −13.34 (dd, $^2J_{H-P}$=22.8 Hz, J=3.8 Hz, 1H); $^{13}$C NMR (125 MHz, CDCl$_3$) δ 167.9 (d, $J_{C-P}$=9.3 Hz), 162.5 (d, J=6.3 Hz), 162.3 (q, $^1J_{C-B}$=50.2 Hz), 160.3 (d, $J_{C-P}$=3.8 Hz), 153.1 (d, $J_{C-P}$=7.8 Hz), 141.6 (d, $J_{C-P}$=1.4 Hz), 136.5 (d, $J_{C-P}$=1.7 Hz), 134.8 (br), 129.0 (qq, $^2J_{C-F}$=31.5 Hz, $^4J_{C-F}$=2.8 Hz), 125.6 (q, $^1J_{C-F}$=272.7 Hz), 117.7 (d, $J_{C-P}$=9.5 Hz), 117.4 (sept, $^3J_{C-F}$=4.1 Hz), 111.1, 106.7 (d, $J_{C-P}$=3.8 Hz), 105.6 (d, $J_{C-P}$=5.4 Hz), 104.3 (d, $J_{C-P}$=38.2 Hz), 101.2 (t, $J_{C-P}$=2.3 Hz), 95.2 (t, $J_{C-P}$=1.9 Hz, COD, CH), 93.7 (d, $J_{C-P}$=29.0 Hz, COD, CH), 68.0 (d, $J_{C-P}$=1.9 Hz, COD, CH), 65.3 (d, $J_{C-P}$=3.6 Hz, COD, CH), 61.6 (dd, J=57.0, 0.8 Hz, CH$_2$O), 55.7, 34.2 (dd, $J_{C-P}$=24.8, 0.8 Hz), 32.8 (d, $J_{C-P}$=4.5 Hz, COD, CH$_2$), 31.7 (COD, CH$_2$), 26.3 (d, J=3.6 Hz, COD, CH$_2$), 25.8 (COD, CH$_2$), 25.4 (d, $J_{C-P}$=3.6 Hz); $^{31}$P NMR (200 MHz, CDCl$_3$) δ 46.45 (d, J=6.5 Hz); HRMS (ESI) m/z 632.1863 (M$^+$), calc. for [IrC$_{26}$H$_{34}$NO$_3$P]$^+$ 632.1900; 863.0648 (BArF), calc. for [C$_{32}$H$_{12}$BF$_{24}$]$^-$ 863.0654.

Complex 7f

The mixture is stirred at room temperature for 30 min after addition of NaBArF. Complete conversion is observed by $^{31}$P NMR. Compound 7f (404 mg) is isolated as a light yellow solid (79% yield). $^1$H NMR (400 MHz, CDCl$_3$) δ 8.22 (dd, J=7.9, 5.4 Hz, 1H), 7.96 (dd, J=8.4, 1.3 Hz, 1H), 7.87 (t, J=7.8 Hz, 1H), 7.79 (td, J=7.8, 1.7 Hz, 1H), 7.69 (br s, BArF), 7.62 (dd, J=7.4, 1.4 Hz, 1H), 7.52 (m, 2H), 7.49 (br s, BArF), 7.36 (t, J=7.8 Hz, 1H), 6.69-6.74 (m, 2H), 6.59 (d, J=6.3 Hz, 1H), 4.85-4.91 (m, 1H), 4.45-4.49 (m, 2H), 3.99 (s, 3H), 3.19 (br t, J=8.1 Hz, 1H), 2.74-2.80 (m, 1H), 2.33-2.43 (m, 2H), 1.88-2.06 (m, 2H), 1.61-1.63 (m, 1H), 1.20 (d, J=17.6 Hz, 9H), 0.82-1.04 (m, 2H), −13.09 (d, $^2J_{H-P}$=19.4 Hz, 1H); $^{13}$C NMR (100 MHz, CDCl$_3$) δ 166.4 (d, $J_{C-P}$=6.3 Hz), 162.6 (d, $J_{C-P}$=6.8 Hz), 161.5 (q, $^1J_{C-B}$=50.0 Hz), 160.2 (d, $J_{C-P}$=3.6 Hz), 156.3 (d, $J_{C-P}$=9.3 Hz), 149.6, 148.9, 145.2, 139.7, 137.6, 136.8 (d, $J_{C-P}$=1.4 Hz), 134.7 (br), 131.9 (d, $J_{C-P}$=5.0 Hz), 129.3 (qq, $^2J_{C-F}$=31.2 Hz, $^4J_{CF}$=3.0 Hz), 127.3 (d, $J_{C-P}$=2.8 Hz), 125.8 (q, $^1J_{C-F}$=272.6 Hz), 124.7, 122.7 (d, $J_{C-P}$=9.3 Hz), 121.4, 117.4 (sept, $^3J_{C-F}$=3.9 Hz), 106.9 (d, $J_{C-P}$=3.7 Hz), 105.9 (d, $J_{C-P}$=5.2 Hz), 105.4, 104.8 (d, $J_{C-P}$=38.7 Hz), 93.1 (d, $J_{C-P}$=29.4 Hz, COD, CH), 92.1 (COD, CH), 73.8 (d, $J_{C-P}$=1.5 Hz, COD, CH), 72.0 (d, $J_{C-P}$=4.0 Hz, COD, CH), 55.8, 34.6 (d, $J_{C-P}$=24.6 Hz), 34.3 (d, $J_{C-P}$=5.2 Hz, COD, CH$_2$), 29.1 (COD, CH), 29.0 (COD, CH), 25.3 (COD, CH), 25.2 (d, $J_{C-P}$=3.6 Hz); $^{31}$P NMR (160 MHz, CDCl$_3$) δ 49.72 (d, J=4.0 Hz); HRMS (ESI) m/z 678.2071 (M$^+$), calc. for [IrC$_{31}$H$_{36}$NO$_2$P]$^+$ 678.2107; 863.0671 (BArF), calc. for [C$_{32}$H$_{12}$BF$_{24}$]$^-$ 863.0654.

General Asymmetric Hydrogenation Procedure:

A high pressure steel autoclave (HEL CAT 24) with a dry glass insert and a magnetic stir bar are taken into a glove box. The glass insert is loaded with alkene substrate 8a (20 mg, 0.138 mmol), catalyst 7a (4.0 mg, 0.0028 mmol) and 0.5 mL of DCM. The hydrogenation vessel is sealed and taken out of the glove box. The reactor is purged with N$_2$ and then H$_2$, and stirred under appropriate H$_2$ pressure and temperature for 20 h. The reactor is then vented; conversion and enantiomeric excess (ee) of 9a are determined by chiral HPLC.

Use of the Iridium catalysts of the invention in reducing tetrasubstituted carbon-carbon double bond of 2,3 dimethyl-indene, compound 8a, is shown below in Table 1

TABLE 1

| Entry | Catalyst | P (psi) | Temp | % Conversion | er of 9a |
|---|---|---|---|---|---|
| 1 | 7a | 500 | RT | 100% | 84:16 |
| 2 | 7a | 100 | RT | 100% | 88:12 |
| 3 | 7a | 100 | 10° C. | 100% | 89:11 |
| 4 | 7b | 500 | RT | 40% | 72:28 |
| 5 | 7c | 500 | RT | 90% | 88:12 |
| 6 | 7d | 500 | RT | 6% | 77:23 |
| 7 | 7e | 100 | 10° C. | 100% | 89:11 |
| 8 | 7f | 500 | RT | 6% | — |
| 9 | 7g | 500 | RT | 15% | 52:48 |
| 10 | 7h | 500 | RT | 10% | — |

$^a$ 2 mol % of Ir complex

The results summarized in Table 2 show that the exemplary metal complex of the invention, 7c, is efficient for the enantioselective hydrogenation of tri and tetrasubstituted double bonds.

TABLE 2

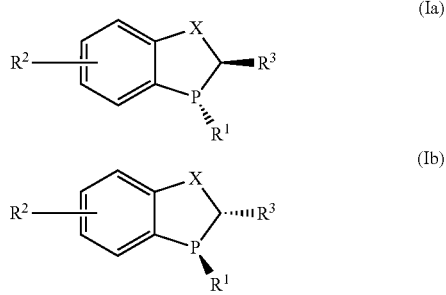

What is claimed is:

1. A compound of formula Ia, Ib, or a mixture thereof:

(Ia)

(Ib)

wherein:

X is O, S, or —NR$^5$;

R$^1$ is —(C$_1$-C$_6$)alkyl, —CF$_3$, —(C$_3$-C$_{10}$)carbocyclyl, -(5- to 11-membered)heterocarbocyclyl, —(C$_6$-C$_{14}$)aryl, -(5 to 11-membered)heteroaryl, or ferrocenyl; wherein said —(C$_3$-C$_{10}$)carbocyclyl, -(5- to 11-membered)heterocarbocyclyl, —(C$_6$-C$_{14}$)aryl and -(5 to 11-membered) heteroaryl of said R$^1$ is optionally substituted with 1 to 3 substituents independently selected from —O(C$_1$-C$_6$) alkyl, —(C$_1$-C$_6$)alkyl, and —CF$_3$;

R$^2$ is H, —O(C$_1$-C$_6$)alkyl, —(C$_1$-C$_6$)alkyl, —(C$_3$-C$_{10}$)carbocyclyl, -(5- to 11-membered)heterocarbocyclyl, —(C$_6$-C$_{14}$)aryl, -(5 to 11-membered)heteroaryl, —NR$^5$R$^6$, or —SR$^5$; wherein said —(C$_3$-C$_{10}$)carbocyclyl, -(5- to 11-membered)heterocarbocyclyl, —(C$_6$-C$_{14}$)aryl, and -(5 to 11-membered)heteroaryl of said R$^2$ is optionally substituted with 1 to 3 substituents independently selected from —O(C$_1$-C$_6$)alkyl, —(C$_1$-C$_6$)alkyl, and —CF$_3$;

R$^3$ is —(C$_1$-C$_6$)alkyl substituted with 1 to 3 (5- to 6-membered)heteroaryl; wherein the (5- to 6-membered)heteroaryl ring is optionally substituted with 1 to 3 R$^4$ substituents independently selected from —O(C$_1$-C$_6$) alkyl, —N—(C$_1$-C$_6$ alkyl)$_2$, —(C$_1$-C$_6$)alkyl, phenyl, (5- to 11-membered)heteroaryl and —CF$_3$;

or

R$^3$ is selected from the group consisting of ortho-substituted pyridine, oxazoline, and chiral oxazoline, wherein each of said ortho-substituted pyridine, oxazoline, and chiral oxazoline is optionally substituted with 1 to 3 R$^4$ substituents independently selected from —O(C$_1$-C$_6$) alkyl, —N—(C$_1$-C$_6$ alkyl)$_2$, —(C$_1$-C$_6$)alkyl, phenyl, (5- to 11-membered)heteroaryl and —CF$_3$;

R$^5$ and R$^6$ are each independently H, —(C$_1$-C$_6$)alkyl, —CF$_3$, —(C$_3$-C$_{10}$)carbocyclyl, -(5- to 11-membered) heterocarbocyclyl, —(C$_6$-C$_{10}$)aryl, or -(5 to 11-membered)heteroaryl; wherein each —(C$_1$-C$_6$)alkyl, —CF$_3$, —(C$_3$-C$_{10}$)carbocyclyl, -(5- to 11-membered)heterocarbocyclyl, —(C$_6$-C$_{10}$)aryl, and -(5 to 11-membered) heteroaryl of said R$^5$ and R$^6$ is optionally independently substituted with 1 to 3 substituents independently selected from halo, —O(C$_1$-C$_6$)alkyl, —(C$_1$-C$_6$)alkyl, and —CF$_3$.

2. The compound according to claim 1, wherein X is O.

3. The compound according to claim 1, wherein X is S.

4. The compound according to claim 1, wherein X is NR$^5$.

5. The compound according to claim 1, wherein R$^1$ is —(C$_1$-C$_6$)alkyl selected from —CH$_3$, —CH$_2$CH$_3$, —CH(CH$_3$)$_2$, —C(CH$_3$)$_3$, —C(CH$_2$CH$_3$)$_3$, and —C(CH$_2$CH$_3$)(CH$_3$)$_2$.

6. The compound according to claim 1, wherein R$^1$ is —(C$_3$-C$_{10}$)carbocyclyl selected from cyclopentyl, cyclohexyl, and 1-adamantyl.

7. The compound according to claim 1, wherein R$^1$ is —(C$_6$-C$_{14}$)aryl selected from phenyl, ortho-tolyl, para-tolyl, 3,5-dimethylphenyl, 3,5-di-t-butylphenyl, 3,5-di-CF$_3$-phenyl, ortho-CF$_3$-phenyl, ortho-anisyl, and naphthyl.

8. The compound according to claim 1, wherein R$^2$ is H, —CH$_3$ or —OCH$_3$.

9. The compound according to claim 1, wherein R$^2$ is phenyl, naphthyl or anthracene, each optionally substituted with 1 to 3 substituents independently selected from —O(C$_1$-C$_6$)alkyl, —(C$_1$-C$_6$)alkyl, and —CF$_3$.

10. The compound according to claim 1, wherein R$^3$ is —(C$_1$-C$_6$)alkyl substituted with 1 to 3 (5- to 6-membered) heteroaryl; wherein the (5- to 6-membered)heteroaryl ring is optionally substituted with 1 to 3 R$^4$ substituents independently selected from —O(C$_1$-C$_6$)alkyl, —(C$_1$-C$_6$)alkyl, phenyl and —CF$_3$.

11. The compound according to claim 10, wherein R$^3$ is —CH$_2$(chiral oxazoline) or —CH$_2$(ortho-substituted pyridine), each optionally substituted with 1 to 3 R$^4$ substituents independently selected from —O(C$_1$-C$_6$)alkyl, —(C$_1$-C$_6$) alkyl, phenyl and —CF$_3$.

12. The compound according to claim 1, wherein R$^3$ ortho-substituted pyridine optionally substituted with 1 to 3 R$^4$ substituents independently selected from —O(C$_1$-C$_6$)alkyl, —(C$_1$-C$_6$)alkyl, phenyl and —CF$_3$.

13. A metal complex of formula (IIa), (IIb), or a mixture thereof:

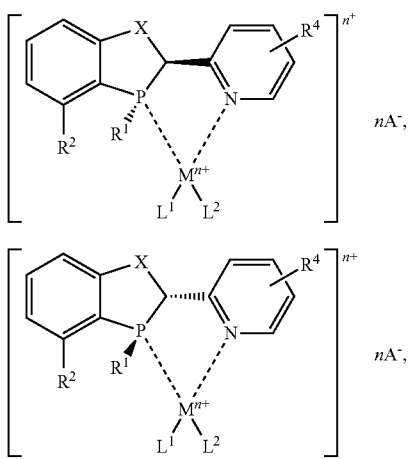

wherein

M is a transition metal selected from Co, Ni, Pd, Pt, Cu, Ag, Au, Ru, Fe, Rh and Ir;

A⁻ is a counter anion;

n is the oxidation state of the transition metal M;

$L^1$ and $L^2$ are each olefins, or $L^1$ and $L^2$ together represent a diolefin;

X is O, S, or —NR⁵;

$R^1$ is —($C_1$-$C_6$)alkyl, —$CF_3$, —($C_3$-$C_{10}$)carbocyclyl, -(5- to 11-membered)heterocarbocyclyl, —($C_6$-$C_{14}$)aryl, -(5 to 11-membered)heteroaryl, or ferrocenyl; wherein said —($C_3$-$C_{10}$)carbocyclyl, -(5- to 11-membered)heterocarbocyclyl, —($C_6$-$C_{14}$)aryl and -(5 to 11-membered) heteroaryl of said $R^1$ is optionally substituted with 1 to 3 substituents independently selected from —O($C_1$-$C_6$)alkyl, —($C_1$-$C_6$)alkyl, and —$CF_3$;

$R^2$ is H, —O($C_1$-$C_6$)alkyl, —($C_3$-$C_{10}$)carbocyclyl, -(5- to 11-membered)heterocarbocyclyl, —($C_6$-$C_{14}$)aryl, -(5 to 11-membered)heteroaryl, —NR⁵R⁶, or —SR⁵; wherein said —($C_3$-$C_{10}$)carbocyclyl, -(5- to 11-membered)heterocarbocyclyl, —($C_6$-$C_{14}$)aryl, and -(5 to 11-membered)heteroaryl of said $R^2$ is optionally substituted with 1 to 3 substituents independently selected from —O($C_1$-$C_6$)alkyl, —($C_1$-$C_6$)alkyl, and —$CF_3$;

$R^4$ is selected from —O($C_1$-$C_6$)alkyl, —($C_1$-$C_6$)alkyl, phenyl and —$CF_3$;

$R^5$ and $R^6$ are each independently H, —$CF_3$, —($C_3$-$C_{10}$)carbocyclyl, -(5- to 11-membered)heterocarbocyclyl, ($C_6$-$C_{10}$)aryl, or -(5 to 11-membered)heteroaryl; wherein each —($C_1$-$C_6$)alkyl, $CF_3$, —($C_3$-$C_{10}$)carbocyclyl, -(5- to 11-membered)heterocarbocyclyl, —($C_6$-$C_{10}$)aryl, and -(5 to 11-membered)heteroaryl of said $R^5$ and $R^6$ is optionally independently substituted with 1 to 3 substituents independently selected from halo, —O($C_1$-$C_6$)alkyl, —($C_1$-$C_6$)alkyl, and —$CF_3$.

14. The metal complex according to claim 13, wherein M is Ir and n is 1.

15. The metal complex according to claim 13, wherein A⁻ is, $BF_4^-$, $SbF_6^-$, TfO⁻, $B(C_6H_5)_4^-$, $B[3,5-(CF_3)_2C_6H_3]_4^-$ (BArF⁻), or $PF_6^-$.

16. The metal complex according to claim 13, wherein M is Ir, A⁻ is BArF⁻, and n is 1.

17. The metal complex according to claim 13, wherein $R^1$ is —$C(CH_3)_3$, and $R^2$ is —$OCH_3$, or —($C_6$-$C_{14}$)aryl; wherein said —($C_6$-$C_{14}$)aryl is optionally substituted with 1 to 3 substituents independently selected from —O($C_1$-$C_6$)alkyl, —($C_1$-$C_6$)alkyl, and —$CF_3$.

18. The metal complex according to claim 13, wherein $L^1$ and $L^2$ together represent a diolefin selected from norbornadiene and cyclooctadiene.

19. The metal complex according to claim 13, wherein the metal complex is of formula (IIa).

* * * * *